United States Patent [19]

Jones et al.

[11] 4,276,298

[45] Jun. 30, 1981

[54] 2-ARYL-1,2-BENZISOTHIAZOLINONE-1,1-DIOXIDES AND THEIR USE AS SELECTIVE PROTEASE INHIBITORS

[75] Inventors: Howard Jones, Holmdel, N.J.; Robert L. Clark, Sequim, Wash.; Morris Zimmerman, Watchung, N.J.

[73] Assignee: Merck & Co., Inc., Rahway, N.J.

[21] Appl. No.: 71,145

[22] Filed: Sep. 6, 1979

Related U.S. Application Data

[63] Continuation-in-part of Ser. No. 889,762, Mar. 24, 1978, abandoned.

[51] Int. Cl.$^3$ .......................................... C07D 275/04
[52] U.S. Cl. ..................................... 424/270; 548/210
[58] Field of Search ................................ 548/211, 210

[56] References Cited

U.S. PATENT DOCUMENTS

4,006,007  2/1977  Bollinger ............................... 71/72

FOREIGN PATENT DOCUMENTS

2636599  3/1977  Fed. Rep. of Germany ........... 548/210
848130   9/1960  United Kingdom .

OTHER PUBLICATIONS

Bambas; Lewis L., "Chemistry of Heterocyclic Compound", vol. 4, pp. 330-339, Interscience Publishers, (1952).

Fischer; Rand H. Hurni, "Arzneitmittel Forschung ", 14, (12), 1301, (1964).

Stroud, "A Family of Protein-Cutting Proteins", *Sci Am*, Jul., 1974, pp.74-78.

Erichson, Acta. Med. Scand. 1964, 175, 197.

*Primary Examiner*—Nicholas S. Rizzo
*Attorney, Agent, or Firm*—Mario A. Monaco; Raymond M. Speer; Thomas E. Arther

[57] ABSTRACT

The invention concerns novel 2-aryl-1,2-benzisothiazolinone-1,1-dioxide compounds; methods for their preparation; pharmaceutical compositions containing them as an active ingredient; and methods of inhibiting proteases, especially elastase, and of treating emphysema, rheumatoid arthritis, and various inflammatory diseases, for example, bronchial inflammation.

10 Claims, No Drawings

2-ARYL-1,2-BENZISOTHIAZOLINONE-1,1-DIOXIDES AND THEIR USE AS SELECTIVE PROTEASE INHIBITORS

This is a continuation-in-part of application Ser. No. 889,762, filed Mar. 24, 1978 now abandoned.

BACKGROUND OF THE INVENTION

1. Field of the Invention

The present invention relates to novel 2-aryl-1,2-benzisothiazolinone-1,1-dioxide compounds and methods of selectively inhibiting proteases especially elastase, and of treating emphysema and rheumatoid arthritis and other inflammatory diseases using the novel compounds.

2. Description of the Prior Art

Various 2-aryl-1,2-benzisothiazolinone-1,1-dioxide compounds have been prepared in the past. Louis L. Bambas, Chemistry of Heterocyclic Compounds, Vol. 4, pp. 330–339, *Interscience Publishers* (1952), discloses 2-phenyl-, 2-(4-nitrophenyl)-, 2-phenylsulfonyl-, 2-(2-chlorocyclohexyl)-, and 2-(2-,3-, and 4-tolyl)-1,2-benzisothiazolinone-1,1-dioxide. However, none of these 2-aryl-1,2-benzisothiazolinone-1,1-dioxide compounds is the same as the compounds of the present invention, and they do not have and would not suggest the activity of the compounds of the present invention in methods of selectively inhibiting proteases, especially elastase, and of treating emphysema, rheumatoid arthritis, and other inflammatory diseases.

R. Fischer and H. Hurni, in "On Benzisothiazolones: A Series with a Wide Range of Bacteriostatic and Fungistatic Activity", *Arzneimittel Forschung*, 14 (12) 1301 (1964), disclose a large number of benzisothiazolones. However, none of these benzisothiazolones are 1,1-dioxide compounds, and they are thus not the same as the compounds of the present invention. Moreover, they do not have and would not suggest the activity of the compounds of the present invention in methods of selectively inhibiting proteases, especially elastase, and of treating emphysema, rheumatoid arthritis, and other inflammatory diseases.

German Offenlegungsschrift No. 26 36 599 discloses certain acyl saccharins and methods of inhibiting elastase and treating emphysema with such compounds. However, those acyl saccharin compounds are not the same as the compounds of the present invention, and it is unexpected that the compounds of the present invention are more stable compounds and provide a greater degree of specificity of protease inhibition activity, which is therapeutically valuable.

BACKGROUND OF THE INVENTION

Possibly a number of different proteases, or proteolytic enzymes, are involved in the initiation and perpetuation of the connective tissue destruction which occurs during the typical inflammatory response of various animals, including humans.

The proteases are an important family of enzymes within the proteolytic enzyme group whose members are essential to a variety of biological activities, such as digestion, formation and dissolution of blood clots, the immune reaction to foreign cells and organisms, and the fertilization of the ovum by the spermatozoon. The proteolytic or protein cutting enzymes are proteins whose function is to alter or decompose other proteins by splitting them into fragments.

Elastase is one of the proteases and it acts on bonds in the middle of the protein chain which are adjacent to aliphatic amino acids. Elastase is of particular interest because it has the broadest spectrum of activity against natural substrates. In particular, the elastase of the granulocyte is important because granulocytes participate in acute inflammation and in acute exacerbation of chronic forms of inflammation, which characterizes many clinically important inflammatory diseases. Granulocyte elastase can attack elastin, proteoglycan, and collagen of connective tissue, activate $C_5$ to release $C_{5a}$, a potent chemotactic factor, and generate Kinin from Kininogen. Also, an elastase has been reported to be a significant secretory product of activated macrophages, a cell type predominating in the chronic phase of inflammation.

Proteases may be inactivated by inhibitors which block the active site of the enzyme by binding tightly thereto. Naturally occurring protease inhibitors form part of the control or defense mechanisms that are crucial to the well-being of the organism, as the protease enzymes would destroy any protein within reach, including themselves. The naturally occurring enzyme inhibitors have evolved a configuration in the binding region that closely resembles the bound substrate, which is part of the reason they bind to the enzyme so tightly (Stroud, "A Family of Protein Cutting Proteins" *Sci. Am.* July 1974, pp. 74–88).

$\alpha_1$-Antitrypsin, a glycoprotein in human serum, has a wide inhibitory spectrum covering trypsin, chymotrypsin, plasmin, kallikrein, elastase, and thrombin. The marked reduction in serum $\alpha_1$-antitrypsin has been associated with pulmonary emphysema (Erickson, S. "Pulmonary emphysema and alpha$_1$-antitryspin deficiency" *Acta. Med. Scand.* 1964, 175, 197). Subsequent studies have confirmed and extended this observation (Morse et al. "A Community Study of the Relation of Alpha$_1$-Antitrypsin Levels to Obstructive Lung Diseases" *The New England Journal of Medicine*, Vol. 292, No. 6, p. 278, Feb. 6, 1975).

Emphysema has been experimentally induced in laboratory animals by aerosolization into the tracheobronchial tree of the proteolytic enzyme, papain, and more recently by dog polymorphonuclear enriched leukocyte homogenates (Mass et al. "Induction of Experimental Emphysema" *American Review of Respiratory Disease*, Vol. 106, p. 384, 1972). The pathological changes are similar to and closely resemble human pulmonary emphysema. Also, intratracheally instilled elastase produces marked alterations in lung elastin with dilatation of alveolar ducts and alveoli (Johanson et al. "Comparison of elastase, collagenase and papain on lung structure and function" *Amer. Rev. Resp. Dis.* 1971, 103, 908). Papain induced emphysema has been inhibited in the hamster by human $\alpha_1$-antitrypsin (HAAT). Since papain is one of the few proteinases not inhibited by HAAT, it has been found that the HAAT works by inhibiting the elastase-like enzymes released by polymorphonuclear (PMN) leukocytes and alveolar macrophages which invade the hamsters' lungs following exposure (Martorana et al. "Inhibition of Papain-Induced Emphysema in the Hamster by Human Alpha$_1$-Antitrypsin," *Can. J. Physiol. Pharmacol.* Vol. 52, No. 3, pp. 758–759, 1974, and Kaplan et al. "The induction of emphysema with elastase" *Journal of Laboratory and Clinical Medicine*, Vol. 82, No. 3, 349–356, Sept. 1973). Elastase inhibitors may be used in control of elastase-like enzymes released by polymorphonuclear (PMN) leukocytes and alveolar macrophages in emphysema.

In rheumatoid arthritis, antigen/antibody complexes have been demonstrated in the synovial fluid and as cytoplasmic inclusions in leukocytes which are chemotactically attracted to the sites of inflammation (Oronsky et al. "Release of Cartilage Mucopolysaccharide Degrading Neutral Protease from Human Leukocytes", *Journal of Experimental Medicine*, Vol. 138, pp. 461-472, 1973). Polymorphonuclear leukocytes (PMN) enter acute inflammatory exudates to phagocytize the immune reactants or microorganisms. During phagocytosis, PMN enzymes are sometimes released extracellularly. When the extracellular release occurs to a degree sufficient to overwhelm the host inhibitors, tissue damage produced by the PMN substances may greatly diminish their beneficial effects. The major portion of neutral proteolylic activity in humans is usually attributed to elastin-like enzymes (Janoff, "Alanine p-nitrophenyl esterase activity of human leukocyte granules", *Biochemical Journal*, 114; pp. 157-159, 1969).

Accordingly, protease, especially elastase, inhibitors can be used to control tissue damage and undesirable conditions such as edema which occur during the course of various inflammatory diseases and conditions, whether those diseases and conditions are, or are not, of immunological origin. The tissue damage and undesirable conditions are mediated by certain cells at the sites of inflammation which release the proteases, especially elastase, which are the proximate causative agents of the tissue damage and undesirable conditions. Thus, protease, especially elastase, inhibitors are useful in treating emphysema, rheumatoid arthritis, and various inflammatory diseases, for example, bronchial inflammation.

However, an important improvement obtained with the novel 2-aryl-1,2-benzisothiazolinone-1,1-dioxide compounds of the present invention is the selective, or specific, inhibition of certain proteases and elastases, while other proteases and elastases remain virtually unaffected. Particularly, the novel inhibitors of the present invention show excellent inhibition of human PMN (polymorphonuclear leukocyte) elastase and bovine chymotrypsin, while exhibiting almost no inhibition of porcine pancreatic elastase, bovine trypsin, and, in most cases, human PMN cathepsin G, as will be shown in more detail below. [The use of animal proteases and elastases in studying inhibitors, as predictive of activity with human proteases and elastases, is well accepted because of the high degree of homology and similarity of amino acid compositions among the structures involved (*Methods in Enzymology*, Vol. XIX, Academic Press, 1970)].

The ability of the novel inhibitors of the present invention to inhibit PMN (polymorphonuclear leukocyte) elastase while not inhibiting trypsin, for example, is therapeutically valuable. The role of PMN elastase in the destructive phases of emphysema, rheumatoid arthritis, and other inflammatory diseases and conditions has already been described in detail above. Trypsin, on the other hand, is part of an important class of protein-processing hydrolases with various essential roles in human metabolism, whose normal functioning it is desirable not to inhibit (Shaw, "Synthetic Protease Inhibitors Acting by Affinity Labeling", *Proteases and Biological Control*, Cold Spring Harbor Laboratory, pp. 455-465, at 459, 1975). Moreover, it is well understood that among the desirable properties of a synthetic inhibitor is specificity for one or a small number of proteases (Powers et al., "Synthetic Inhibitors of Granulocyte Elastase and Cathepsin G", *Neutral Proteases of Human Polymorphonuclear Leukocytes*, pp. 221-233, 1978; Cohen, *Report of the Working Group for Evaluation of Elastase Inhibitor Replacement Therapy in Pulmonary Emphysema*, pp. 8-9, Oct. 17-18, 1978, Bethesda, Md.; Larsen and Shaw, "Active-Site-Directed Alkylation of Chymotrypsin by Reagents Utilizing Various Departing Groups", *Journal of Medicinal Chemistry*, Vol. 19, No. 11, pp. 1284-1286, 1976; Wong and Shaw, "Inactivation of Trypsin-like Proteases by Active-Site-Directed Sulfonylation", Archives of Biochemistry and Biophysics, 176, pp. 113-118, 1976; Abeles and Maycock, "Suicide Enzyme Inactivators", *Accounts of Chemical Research*, Vol. 9, No. 9, 1976; Kettner and Shaw, "Synthesis of Peptides of Arginine Chloromethyl Ketone", *Biochemistry*, Vol. 17, No. 22, pp. 4778-4783, 1978; Aoyagi, "Structure and Activities of Proteinase Inhibitors of Microbial Origin", *Bioactive Peptides Produced by Microorganisms*, Chapter 7, pp. 129-140, Halstead Press, 1978; and Kuhn and Senior, *Lung*, Vol. 155, p. 191, 1978).

SUMMARY OF THE INVENTION

It has been found that certain novel 2-aryl-1,2-benzisothiazolinone-1,1-dioxide compounds are useful in methods of inhibiting proteases, especially elastase, and of treating emphysema rheumatoid arthritis, and other inflammatory diseases. These methods comprise the administration of a therapeutically effective amount of a compound of the formula:

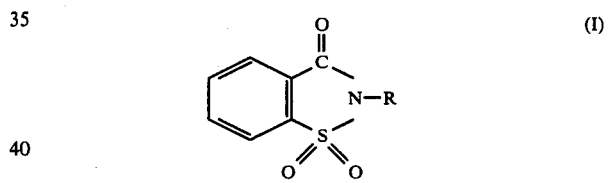

wherein R is

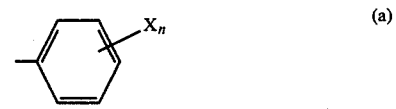

where n is 1 to 5; and X is independently selected from (1) fluoro; (2) nitro, except that where X is only nitro, n must be 2 and X must be 2,4-or 3,5-dinitro; (3) trifluoromethyl; (4) cyano; (5) $C_{1-3}$ alkoxycarbonyl; (6) $C_{1-3}$ alkylcarbonyl; (7) carboxyl; (8) carbamoyl; (9) $C_{1-3}$ alkylacylamino; (10) $C_{1-3}$ alkylsulfonyl; (11) N,N-di($C_{1-3}$ alkyl) sulfamyl; (12) trifluoromethoxy; (13) trifluoromethylthio; and (14) trifluoromethylsulfonyl; and (15) trifluoromethylsulfinyl or

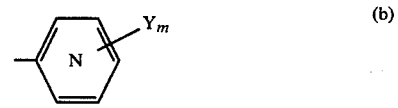

where m has the same meaning as n above, and Y has the same meaning as X, except that it may additionally be mono-nitro.

In a preferred embodiment, n is 1 or 2 and Y is nitro or cyano.

In a more preferred embodiment, n is 2 and X is nitro, trifluoromethyl, or cyano; and n is 5 and X is fluoro.

Representative compounds of the present invention which inhibit proteases, especially elastase, and therefore are useful for treating emphysema, rheumatoid arthritis, and other inflammatory diseases are the following novel compounds:

2-(2,4-dinitrophenyl)-1,2-benzisothiazolinone-1,1-dioxide 2-(2,3,4,5,6-pentafluorophenyl)-1,2-benzisothiazolinone-1,1-dioxide 2-(2-nitro-4-trifluoromethylphenyl)-1,2-benzisothiazolinone-1,1-dioxide 2-(2-cyano-4-nitrophenyl)-1,2-benzisothiazolinone-1,1-dioxide 2-(4-nitro-5-trifluoromethylphenyl)-1,2-benzisothiazolinone-1,1-dioxide 2-(2,4-dicyanophenyl)-1,2-benzisothiazolinone-1,1-dioxide 2-(3,5-dinitrophenyl)-1,2-benzisothiazolinone-1,1-dioxide 2-(3-nitropyrid-2-yl)-1,2-benzisothiazolinone-1,1-dioxide 2-(5-nitropyrid-2-yl)-1,2-benzisothiazolinone-1,1-dioxide 2-(5-cyanopyrid-2-yl)-1,2-benzisothiazolinone-1,1-dioxide 2-(3,5-dinitropyrid-2-yl)-1,2-benzisothiazolinone-1,1-dioxide The present invention is also concerned with novel methods of inhibiting proteases, especially elastase, and of treating emphysema, rheumatoid arthritis and other inflammatory diseases which comprise administering to a patient in need of such treatment a therapeutically effective amount of a compound of Formula I.

The present invention is still further concerned with novel pharmaceutical compositions comprising a non-toxic pharmaceutically acceptable carrier and a compound of Formula I.

The inhibition of proteases, especially elastase, and the treatment of emphysema, rheumatoid arthritis and other inflammatory diseases in accordance with the methods of the present invention is accomplished by orally, rectally, parenterally, or topically administering to patients the compounds of Formula I, or mixtures thereof, in a nontoxic pharmaceutically acceptable carrier.

The non-toxic pharmaceutically acceptable carrier may be, for example, either a solid or a liquid. Exemplary of solid carriers are lactose, corn starch, gelatin, talc, stearic acid, magnesium stearate, terra alba, sucrose, agar, pectin and acacia. Exemplary of liquid carriers are peanut oil, olive oil, sesame oil and water. Similarly, the carrier or diluent may include a time delay material such as glyceryl monostearate or glyceryl distearate, alone, or with a wax.

Different pharmaceutical forms of the therapeutically useful compositions of the present invention may be utilized for administration. For example, if a solid carrier is used, the compositions may take the form of tablets, capsules, powders, troches or lozenges, prepared by standard pharmaceutical techniques. If a liquid carrier is used, the preparation may be in the form of a soft gelatin capsule, a syrup, a liquid solution, a liquid emulsion, or a liquid suspension, or a liquid which may be sprayed by aerosol or nebulizer. Suppositories may be prepared in the conventional manner by mixing the compounds of Formula I with a suitable non-irritating excipient which is solid at room temperature. Exemplary of such excipients are cocoa butter and polyethylene glycol. Gels, lotions and aerosol sprays for topical application may be prepared in conventional manner.

The active compounds are administered in a therapeutically effective amount sufficient to inhibit proteases, especially elastase. The treatment of emphysema is one condition where the inhibition of elastase will arrest the condition, and accordingly the amount of active compound necessary to inhibit elastase is the amount required to treat emphysema. Advantageously, the active compounds will be administered, alone or in a pharmaceutical composition, in an amount of from about 1.0 mg. to 100 mg. per kilogram of body weight per day (50 mg. to 5.0 g. per patient per day) of the active compound, preferably from about 1.5 mg. to 15 mg. per kilogram of body weight per day. The daily dosage may be given in either single or multiple dosages.

The methods of treatment of the present invention comprise administering to a patient (human or animal) a compound of Formula I admixed with a non-toxic pharmaceutically acceptable carrier such as exemplified above. It should be understood that although preferred dosage ranges are given, the dosage level for any particular patient depends upon the activity of the specific compound employed. Also, many other factors that modify the actions of drugs will be taken into account by those skilled in the art of therapeutic use of medicinal agents, for example, body weight, sex, diet, time of administration, route of administration, rate of excretion, drug combination, reaction sensitivities, and severity of the particular disease.

The present invention is also concerned with novel compounds of the formula:

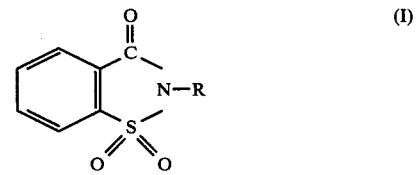

where R has the same meaning as above.

Preferred compounds are those wherein n is 1 or 2 and Y is nitro or cyano.

More preferred compounds are those wherein n is 2 and X is nitro, trifluoromethyl, or cyano, and wherein n is 5 and X is fluoro.

The present invention is still further concerned with a method of preparing the novel compounds of Formula I, by carrying out a series of reactions which may be represented by the following equations:

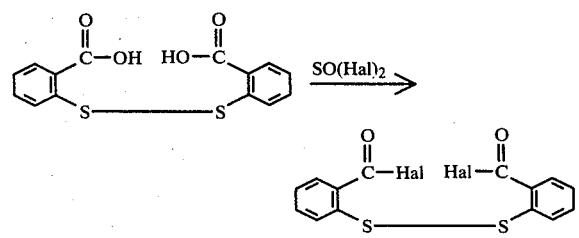

-continued

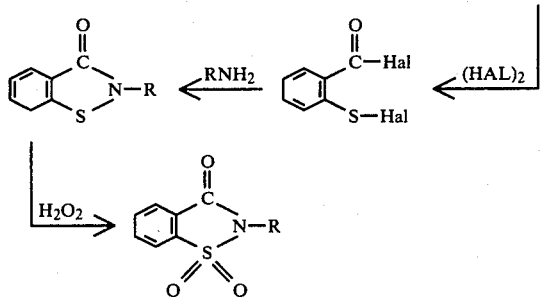

where R has the same meaning as above, and Hal is chloro, bromo, or iodo, preferably chloro.

In the first reaction step, 2,2'-dithiodibenzoic acid disulfide is treated with an agent for producing an acid chloride, such as thionylchloride. Other agents which may be employed include a phosphorous trihalide, a phosphorous pentahalide, a phosphorous oxytrihalide, and phosgene. Preferably, a thionyl halide is used, either by itself or in an inert solvent. The inert solvent may be a hydrocarbon such as toluene, xylene, and especially benzene. The mixture of 2,2'-dithiodibenzoic acid and thionylchloride is refluxed with stirring until the reaction is essentially complete.

In the second reaction step, halogenation may be carried out in an inert solvent which may be selected from chlorinated hydrocarbons such as methylene chloride, chloroform and carbon tetrachloride, or hydrocarbons such as benzene. The halogenating agent may be N-chlorosuccinimide, N-bromosuccinimide, an organic hypohalite such as t-butyl hypochlorite, liquid bromine, or preferably chlorine gas. The halogenation may be carried out at a temperature of from about 0° C. to 100° C., preferably at ambient temperatures. The time of reaction is not critical and the reaction is preferably carried out until it is essentially complete. The pressure is not critical and the halogenation is generally carried out at atmospheric pressure in an open system. The 2-halothiobenzoyl halide which is produced may be recovered in a conventional manner, such as by crystallization and filtration.

In the third reaction step the 2-halothiobenzoyl halide is reacted with a compound of the formula:

R—NH$_2$ where R is as defined above. The reaction between these compounds, an intermolecular cyclization, may be carried out in an aprotic solvent which may be a hydrocarbon such as benzene, an ether such as diethyl ether or tetrahydrofuran, an amide such as dimethylformamide, or a halogenated hydrocarbon such as methylene chloride, chloroform, or carbon tetrachloride. The reaction may be carried out in the presence of a mild base, which may be an alkali metal carbonate such as sodium carbonate, an alkaline earth metal carbonate such as calcium carbonate, an alkali metal bicarbonate such as sodium bicarbonate, an alkaline earth metal bicarbonate such as calcium bicarbonate, a tertiary amine such as triethylamine, or a pyridine. The mild bases which are liquids at ambient temperatures may also be used in excess as the solvent. The reaction may be carried out between 0° and 150° C., preferably at ambient temperatures. The time of reaction is not critical and the reaction is preferably carried out until it is essentially complete. The pressure is not critical and the reaction is generally carried out at atmospheric pressure in an open system. The 2-aryl-1,2-benzisothiazolinone which is produced may be recovered in a conventional manner, such as by crystallization and filtration.

In the fourth and final reaction step the 2-aryl-1,2-benzisothiazolinone is oxidized to produce the compounds of Formula I. This oxidation may be accomplished with an appropriate oxidizing agent such as hydrogen peroxide or potassium permanganate, and is carried out in any alkanoic acid solvent, from ambient temperature to 120° C.

The following examples will serve to illustrate the manner in which the compounds and compositions of the present invention may be prepared. All parts are given in parts by weight unless otherwise expressed.

EXAMPLE 1

2-(2,4-dinitrophenyl)-1,2-benzisothiazolinone-1,1-dioxide

A. 2-(2,4-dinitrophenyl)1,2-benzisothiazolinone

To a stirred suspension of 5.35 g. (0.029 mole) of 2,4-dinitroaniline in 30 ml. of pyridine was added a solution of 6.0 g. (0.029 mole) of 2-chlorothiobenzoyl chloride in 20 ml. of carbon tetrachloride. The temperature rose to 50° C. and after all the addition was complete a precipitate appeared. After one hour the temperature was down to room temperature and the precipitate was removed by filtration. This precipitate was mixed with water which yielded an insoluble gummy material. After washing the gummy material with water the product was crystallized from acetone by the addition of water to give 2.5 g., m.p. 188°-190° C.

B. 2-(2,4-dinitrophenyl)-1,2-benzisothiazolinone-1,1-dioxide

To a solution of 13 ml. of glacial acetic acid and 2.0 ml. of 90% hydrogen peroxide was added 2.0 g. of 2-(2,4-dinitrophenyl)-1,2-benzisothiazolinone. The temperature was gradually raised until the temperature was 100° C., where it was maintained for one hour. After cooling, the mixture was diluted with 20 ml. of water and the precipitate removed by filtration. The precipitate was crystallized from 5 ml. of dimethyl formamide and 5 ml. of acetone by the slow addition of water. The yield of final product was 800 mg., m.p. 225°-226° C.

EXAMPLES 2-19

Following the procedures of Example 1 above, but substituting for the 2,4-dinitroaniline equimolar amounts of the appropriate substituted aniline, there were prepared the 2-R-1,2-benzisothiazolone and 2-R-1,2-benzisothiazolinone-1,1-dioxide compounds depicted in Table I below:

TABLE I

| Example | R | m.p. (°C.) | m.p. (°C.) |
|---|---|---|---|
| 2 | 2,3,4,5,6-pentafluorophenyl | 131–133 | 165–167 |

TABLE I-continued

| Example | R | m.p. (°C.) [sulfide] | m.p. (°C.) [sulfone] |
|---|---|---|---|
| 3 | 2,4-dinitrophenyl | 188–190 | 225–226 |
| 4 | 4-trifluoromethylphenyl | 178–179 | 149–150 |
| 5 | 2-cyano-4-nitrophenyl | 221–222 | 247–248 |
| 6 | 2-nitro-4-trifluoromethylphenyl | 173–174 | 196–197 |
| 7 | 2-methyl-4-nitrophenyl | 157–158 | 200–202 |
| 8 | 4-ethoxycarbonylphenyl | 152–153 | 135–136 |
| 9 | 2-trifluoromethyl-4-nitrophenyl | 136–139 | 184–187 |
| 10 | 3-trifluoromethyl-4-nitrophenyl | 171–172 | 182–183 |
| 11 | 4-carboxyphenyl | 275–285 | 236–238 |
| 12 | 4-(N,N-dimethylsulfamylphenyl | 191–192 | 193–195 |
| 13 | 2-methoxy-4-nitrophenyl | 178–179 | 206–207 |
| 14 | 2,4-dicyanophenyl | 239–240 | 275–276 |
| 15 | 2-cyanophenyl | 182–183 | 209–212 |
| 16 | 3-cyanophenyl | 183–184 | 173–174 |
| 17 | 2-methoxycarbonylphenyl | 110–111 | 219–221 |
| 18 | 3-trifluoromethylphenyl | 131–133 | 103–104 |
| 19 | 3,5-dinitrophenyl | 245–246 | 175–176 |

EXAMPLE 20

2-(5-nitropyrid-2-yl)-1,2-benzisothiazolinone-1,1-dioxide

A. 2-chlorothiobenzoyl chloride

To a reaction flask equipped with a stirrer was added 20 g. of 2,2'-dithiodibenzoylchloride disulfide and 160 ml. of carbon tetrachloride. Chlorine gas was passed to the reaction mixture for 40 minutes, after which the reaction mixture was filtered, the solvent removed, and the product crystallized. The product was then redissolved in carbon tetrachloride and diluted up to 80 ml.

B. 2-(5-nitropyrid-2-yl)-1,2-benzisothiazolinone

To a reaction flask was added 4.1 g. of 2-amino-5-nitropyridine, 15 ml. of pyridine and 20 ml. of the solution of 2-chlorothiobenzoyl chloride prepared in Step A. 20 ml. of carbon tetrachloride were then added and the reaction mixture was heated to 60° C. for 15 minutes with stirring. The reaction mixture was slowly cooled and the precipitate which formed was separated by filtration, and 7 g. were recovered, m.p. 317°–318° C.

C. 2-(5-nitropyrid-2-yl)-1,2-benzisothiazolinone-1,1-dioxide

To a reaction flask was added 2 g. of the 2-(4-nitropyrid-2-yl)-1,2-benzisothiozolinone prepared in Step B., 13 ml. of acetic acid, and 2 ml. of 90% hydrogen peroxide solution. The reaction mixture was heated slowly to 100° C. and then slowly cooled, after which water was added and the reaction mixture was filtered. The 300 mg. of product had a m.p. of 275°–277° C. The product was then crystallized from acetone and found to have a m.p. of 279°–280° C.

EXAMPLES 21–23

The procedures of Example 20 above was followed, except that there was substituted for the 2-amino-5-nitropyridine employed therein, equimolar amounts of the appropriate 2-aminopyridine necessary to produce the compounds set out in Table II below.

TABLE II

| Example | R | m.p. (°C.) [sulfide] | m.p. (°C.) [sulfone] |
|---|---|---|---|
| 21 | 3-nitropyrid-2-yl | 224–225 | 216–219 |
| 22 | 5-cyanopyrid-2-yl | 302–303 | 249–250 |
| 23 | 3,5-dinitropyrid-2-yl | 239–240 | 224–226 |

As described above, the 2-aryl-1,2-benzisothiazolinone-1,1-dioxide compounds of the present invention may be prepared by oxidation of the corresponding 2-aryl-1,2-benzisothiazolinone compounds, using, for example, hydrogen peroxide in acetic acid as the oxidizing agent.

Another method of preparing the 2-aryl-1,2-benzisothiazolinone-1,1-dioxide compounds of the present invention which may be employed comprises the steps of (1) reacting an appropriately substituted aniline with o-sulfobenzoic acid cyclic anhydride; and (2) heating the product of step (1) in polyphosphoric acid at a temperature of from 180°–220° C. to give the desired product. These reactions are illustrated in the following scheme:

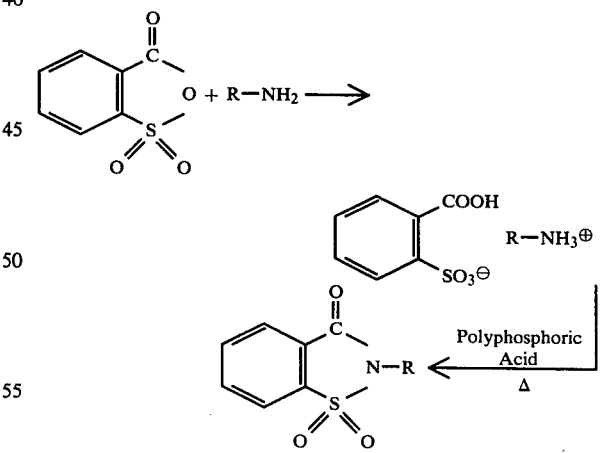

where R has the same meaning as described further above.

Yet another method of preparing the 2-aryl-1,2-benzisothiazolinone-1,1-dioxide compounds of the present invention comprises the steps of (1) heating an appropriately substituted aniline with o-sulfobenzoic cyclic anhydride in the presence of phosphorus oxychloride; and (2) refluxing the product of step (1) in hydrochloric acid to give the desired product. These reactions are illustrated in the following scheme:

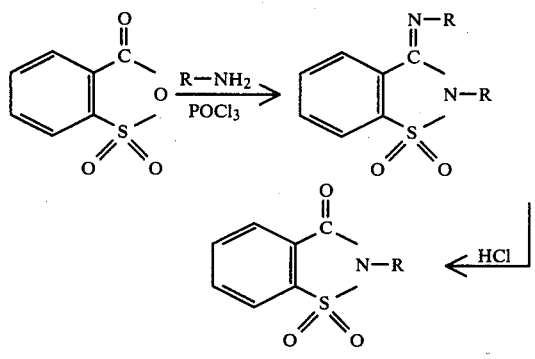

The following examples will serve to illustrate the manner in which the above methods of preparation may be carried out.

EXAMPLE 24

2-(2,3,4,5,6-pentafluorophenyl)-1,2-benzisothiazolinone-1,1-dioxide

To a solution of 10 g. (0.054 mole) of o-sulfobenzoic acid cyclic anhydride in 75 ml. of warm dioxane was added 10 g. (0.054 mole) of 2,3,4,5,6-pentafluoroaniline. A precipitate immediately appeared. After warming on a steam bath for 15 hrs., the reaction mixture was cooled to room temperature and the precipitate was then washed with ether to give 14 g. (75% yield) of the salt. A mixture of 3 G. of the salt and 15 ml. of polyphosphoric acid was immersed in a silicone bath heated at 200° C. After 7 min. the solution was cooled slightly and diluted with 50 ml. of water. The precipitate was removed by filtration. After several runs of this size the combined precipitate weighed 3.0 g. (16% yield). This was recrystallized from 40 ml. of acetone by the slow addition of about 7 ml. of water. Total yield was 15% (2.8 g.), and the product m.p. was 168°–169° C.

EXAMPLE 25

2-(4-fluorophenyl)-1,2-benzisothiazolinone-1,1-dioxide

A.

N-[2-(4-fluorophenyl)-1,2-benzisothiazol-3(2H)-ylidene]benzenamine-S,S-dioxide

To a suspension of 5.52 g. (0.03 mole) of o-sulfobenzoic cyclic anhydride in 35 ml. of phosphorus oxychloride is added, in portions, 6.73 g. (0.06 mole) of p-fluoroaniline over 5 min. The reaction gets warm and a clear solution results. This solution is heated under reflux for 2 hrs. and then the excess phosphorus oxychloride is removed in vacuo. The thick residue is stirred with 150 ml. of ice water until a filterable solid is formed. Filtration separates the solid which is then dissolved in 75 ml. of chloroform and diluted with ether to the cloud point. The solution is filtered through diatomaceous earth, after which petroleum ether is added to the filtrate, which causes crystallization of the final product.

B.

2-(4-fluorophenyl)-1,2-benzisothiazolinone-1,1-dioxide

A mixture of 1.5 g. of the compound prepared in Step A. above is stirred and heated under reflux with 60 ml. of concentrated hydrochloric acid for 2.5 hrs. A solid is always found to be present. After cooling, the solid is removed by filtration.

The selective inhibition of proteases, especially elastase, provided by the novel 2-aryl-1,2-benzisothiazolinone-1,1-dioxide compounds of the present invention was evaluated with respect to several proteases and elastases, and was compared with the inhibiting activity of a related compound of Bambas, and the acyl saccharins of German Offen. No. 26 36 599, mentioned previously. The results of those evaluations, as well as the procedures employed, are set forth in the following example.

EXAMPLE 26

Procedure

HUMAN PMN ELASTASE:
Reagents:
N-tris (hydroxymethyl) methyl-2-aminoethane sulfonic acid
0.2 mM N-t-Box-Alanyl-Alanyl-Prolyl-Alanine-p-nitroanilide=Boc-AAPAN
To prepare substrate, the solid (m.w. 550) was first dissolved in 10.0 ml. DMSO. Buffer at pH 7.5 was then added to a final volume of 100 ml.
Crude extract of human polymorphonuclear leukocytes (PMN) containing elastase activity.
Inhibitors to be tested dissolved in DMSO just before use.
Assay Procedure:
To 1.0 ml. of 0.2 mM Box-AAPAN in a cuvette, 0.01–0.1 ml. of DMSO with or without inhibitor was added. After mixing, a measurement was taken at 410 m$\mu$ to detect any spontaneous hydrolysis due to presence of test compound. 0.05 ml. of PMN extract was then added and the $\Delta$OD/min at 410 m$\mu$ was measured and recorded. A Gilford 240 or Beckman DB-G spectrophotomer was used.
Results:
Results were obtained as % inhibition produced by test compound as represented by the % decrease in $\Delta$OD/min. of a control. The ID$_{50}$ was then derived from the % inhibition curve.
Comments:
The elastase activity in the crude PMN extract may vary from one preparation to another. A control of each new batch is run and the volume added in the assay procedure is adjusted according to activity.
PORCINE PANCREATIC ELASTASE:
Reagents:
N-tris (hydroxymethyl) methyl-2-aminoethane sulfonic acid
0.2 mM N-t-Box-Alanyl-Alanyl-Prolyl-Alanine-p-nitroanilide=Boc-AAPAN
To prepare substrate, the solid (m.w. 550) was first dissolved in 10.0 ml. DMSO. Buffer at pH 7.5 was then added to a final volume of 100 ml.
Solution of purified porcine pancreatic elastase (PPE) (Worthington)
Inhibitors to be tested dissolved in DMSO just before use.
Assay Procedure:
To 1.0 ml. of 0.2 mM Box-AAPAN in a cuvette, 0.01–0.1 ml. of DMSO with or without inhibitor was added. After mixing, a measurement was taken at 410 m$\mu$ to detect any spontaneous hydrolysis due to presence of test compound. 0.05 ml. of PPE extract was then added and the $\Delta$OD/min at 410 m° was measured and recorded. A Gilford 240 or Beckman DB-G spectrophotometer was used.

Results:
Results were obtained as % inhibition produced by test compound as represented by the % decrease in ΔOD/min of a control. The $ID_{50}$ was then derived from the % inhibition curve.
Comments:
The elastase activity in the crude PPE extract may vary from one preparation to another. A control of each new batch is run, and the volume added in the assay procedure is adjusted according to activity.
CHYMOTRYPSIN:
Reagents:
0.05 M $K_2HPO_4/KH_2PO_4$ Buffer, pH 7.5
a-Chymotrypsin (Worthington, 3X crystallized, lyophilized) at 100 µg/ml in 0.001 M HCl (1 mg/ml by wt. diluted 1:10)
0.2 mM N-Acetyl-Alanyl-Alanyl-Prolyl-Phenylalanyl-p-nitroanilide=Ac-AAPPhN. To prepare substrate, the solid (M.W. 566) was first dissolved in 10.0 ml DMSO. Buffer at pH 7.5 was then added to a final volume of 100 ml.
Inhibitors to be tested dissolved in DMSO just before use.
Assay Procedure:
To 1.0 ml of 0.2 mM Ac-AAPPhN in a cuvette, 0.01–0.05 ml of DMSO with or without inhibitor was added. After mixing, a measurement was taken at 410 mµ to detect any spontaneous hydrolysis due to the presence of test compound. 0.01 ml of α-chymotrypsin solution was then added and the ΔOD/min at 410 m° was measured and recordeed. A Gilford 240 240 spectrophotometer was used.
Results:
Results were obtained as % inhibition produced by test compound as represented by the % decrease in ΔOD/min of a control. The $ID_{50}$ was then derived from the % inhibition curve.
Comments:
The Km for chymotrypsin with this substrate is $2.3 \times 10^{-4}$ M. This substrate, prepared as described above, is stable in solution for several months when stored at 4° C.
TRYPSIN:
Reference:
Erlanger, B. F., Kokowsky, N., Cohen, W., *Arch. Biochem. Biophys.*, 95, 271–278 (1961).
Reagents:
0.05 M $K_2HPO_4/KH_2PO_4$ Buffer, pH 7.5
Trypsin (Worthington-TRL, 2X crystallized, lyophilized) at 1.0 mg/ml by wt. in 0.001 M HCl.
1.0 mN N-Benzoyl-DL-Arginine-p-nitroanilide (Bachem)=BAPA. The substrate was prepared by dissolving solid (M.W. 435) in 10 ml. DMSO. Buffer, at pH 7.5, was added to a total volume of 100 ml.
Inhibitors dissolved in DMSO just before use.
Assay Procedure:
To 1.0 ml of 1.0 mM BAPA in a cuvette, 0.01–0.05 ml of DMSO with or without inhibitor was added. After mixing, a measurement was taken at 410 mµ to detect any spontaneous hydrolysis due to the presence of test compound. 0.01 ml of trypsin solution was then added and the ΔOD/min at 410 mµ was measured and recorded. A Gilford 240 spectrophotometer was used.
Results:
Results were obtained as % inhibition produced by test compound as represented by the % decrease in ΔOD/min of a control. The $ID_{50}$ was then derived from the % inhibition curve.
HUMAN PMN CATHEPSIN G:
Reagents:
0.05 M PIPES buffer [piperazine-N,N'-bis(2-ethanesulfonic acid), mono-sodium salt, monohydrate], pH 6.5.
0.2 mM t-Box-L-Tyrosine-p-Nitrophenyl ester=BTNP
Purified extract of human polymorphonuclear leukocytes (PMN) containing chymotrypsin-like activity.
Inhibitors to be tested dissolved in DMSO just before use.
Assay Procedure:
To 1.0 ml of 0.2 mM BTNP in a cuvette, 0.01–0.1 ml of DMSO with or without inhibitor was added. After mixing, a measurement was taken at 347.5 mµ to detect any spontaneous hydrolysis due to the presence of test compound. 0.01 ml of PMN extract was then added and the ΔOD/min at 347.5 mµ was measured and recorded. A Gilford 240 or Beckman DB-G spectrophotometer was used.
Results:
Results were obtained as % inhibition produced by test compound as represented by the % decrease in ΔOD/min. of a control. The $ID_{50}$ was then derived from the % inhibition curve.
Comments:
1. To prepare substrate, 8.0 mg of solid (m.w. 402) was first dissolved in 10.0 ml DMSO. Buffer at pH 6.5 was then added to a final volume of 100 ml. Final DMSO concentration was 10%. Substrate prepared in this manner is stable for 3–4 hours at room temperature.
2. All activites were tested for reactivity with nitrophenol. The test is invalid if the test compound reacts with nitrophenol.

RESULTS

Compound

[Structure: benzisothiazolone-1,1-dioxide with N–R substituent]

| R | Human PMN Elastase | Porcine Pancreatic Elastase | $ID_{50}$ (µg./ml.) Chymotrypsin | Trypsin | Human PMN Cathepsin G |
|---|---|---|---|---|---|
| [structure: –C(=O)–O– group] | 0.1 | 0.2 | 0.02 | 0.5 | 0.4 |

RESULTS-continued

Compound:

| R | Human PMN Elastase | Porcine Pancreatic Elastase | ID$_{50}$ (μg./ml.) Chymotrypsin | Trypsin | Human PMN Cathepsin G |
|---|---|---|---|---|---|
|  *a* | 0.1 | 0.2 | 0.2 | 0.02 | 0.4 |
| (CH$_3$CH$_2$)$_2$CH—C(=O)— *a* | 0.1 | 0.3 | 0.04 | 1.0 | 2.0 |
| CH$_2$=CH—C(=O)— *a* | 0.1 | 0.2 | 0.07 | 0.4 | 1.0 |
| O$_2$N—C$_6$H$_4$— *b* | 50 | 100 | 100 | 100 | 100 |
| O$_2$N—C$_6$H$_3$(NO$_2$)— | 1.0 | 50 | 0.5 | 50 | 10 |
| C$_6$F$_5$— | 1.0 | 50 | 50 | 50 | 50 |
| O$_2$N—C$_6$H$_3$(CN)— | 1.0 | 20 | 0.2 | 20 | 15 |
| (NO$_2$)pyridyl— | 0.5 | 20 | 0.2 | 20 | 15 |
| NC—pyridyl— | 3.0 | 50 | 17 | 50 | 50 |
| NC—C$_6$H$_3$(CN)— | 1.5 | 50 | 1.0 | 50 | 50 |

*a* Compounds of German Offen 26 36 599.
*b* Compound of Bambas

What is claimed is:

1. A compound of the formula:

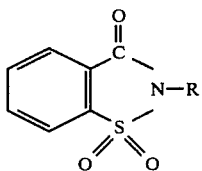

wherein R is

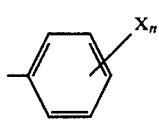   [(a)]

where n is 1 or 2, except where X is fluoro, n may also be up to and including 5; and X is independently selected from (1) fluoro; (2) nitro, except that where X is only nitro, n must be 2 and X must be 2,4- or 3,5-dinitro; (3) trifluoromethyl; (4) cyano; (5) C$_{1-3}$ alkoxycarbonyl; (6) C$_{1-3}$ alkylcarbonyl (7) carboxyl; (8) carbamoyl; (9) C$_{1-3}$ alkylacylamino; (10) C$_{1-3}$ alkylsulfonyl; (11) N,N-di(C$_{1-3}$ alkyl) sulfamyl; (12) trifluoromethoxy; (13) trifluoromethylthio; (14) trifluoromethylsulfonyl; and (15) trifluoromethylsulfinyl.

2. A compound of claim 1 wherein n is 2 and X is nitro, trifluoromethyl, or cyano; or n is 5 and X is fluoro.

3. The compound of claim 1 which is 2-(2,4-dinitrophenyl)-1,2-benzisothiazolinone-1,1-dioxide.

4. The compound of claim 1 which is 2-(2,3,4,5,6-pentafluorophenyl)-1,2-benzisothiazolinone-1,1-dioxide.

5. The compound of claim 1 which is 2-(2-cyano-4-nitrophenyl)-1,2-benzisothiazolinone-1,1-dioxide.

6. The compound of claim 1 which is 2-(2,4-dicyanophenyl)-1,2-benzisothiazolinone-1,1-dioxide.

7. A method of selectively inhibiting proteases, especially elastase, comprising the administraion to a patient of a therapeutically effective amount of a compound of the formula:

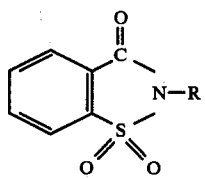

wherein R is

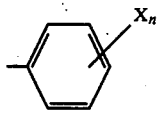 [(a)]

where n is 1 or 2, except where X is fluoro, n may also be up to and including 5; and X is independently selected from (1) fluoro; (2) nitro, except that where X is only nitro, n must be 2 and X must be 2,4- or 3,5-dinitro; (3) trifluoromethyl; (4) cyano; (5) $C_{1-3}$ alkoxycarbonyl; (6) $C_{1-3}$ alkylcarbonyl; (7) carboxyl; (8) carbamoyl; (9) $C_{1-3}$ alkylacylamino; (10) $C_{1-3}$ alkylsulfonyl; (11) N,N-di($C_{1-3}$ alkyl) sulfamyl; (12) trifluoromethylsulfonyl; and (15) trifluoromethylsulfinyl.

8. The method of claim 7 wherein n is 2 and X is nitro, trifluoromethyl, or cyano; or n is 5 and X is fluoro.

9. A pharmaceutical composition for selectively inhibiting proteases, especially elastase, comprising a nontoxic pharmaceutically acceptable carrier and a therapeutically effective amount of a compound of the formula:

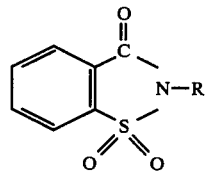

wherein R is

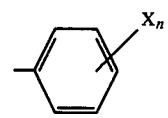

where n is 1 or 2, except where X is fluoro, n may also be up to and including 5; and X is independently selected from (1) fluoro; (2) nitro, except that where X is only nitro, n must be 2 and X must be 2,4- or 3,5-dinitro; (3) trifluoromethyl; (4) cyano; (5) $C_{1-3}$ alkoxycarbonyl; (6) $C_{1-3}$ alkylcarbonyl; (7) carboxyl; (8) cabamoyl; (9) $C_{1-3}$ alkylacylamino; (10) $C_{1-3}$ alkylsulfonyl; (11) N,N-di($C_{1-3}$ alkyl) sulfamyl; (12) trifluoromethoxy; (13) trifluoromethylthio; (14) trifluoromethylsulfonyl; and (15) trifluoromethylsulfinyl.

10. The composition of claim 9 wherein n is 2 and X is nitro, trifluoromethyl, or cyano; or n is 5 and X is fluoro.

* * * * *

UNITED STATES PATENT AND TRADEMARK OFFICE
CERTIFICATE OF CORRECTION

PATENT NO. : 4,276,298
DATED : June 30, 1981
INVENTOR(S) : HOWARD JONES et al

It is certified that error appears in the above—identified patent and that said Letters Patent is hereby corrected as shown below:

Column 18, line 1, after "(12)" insert --- trifluoromethoxy; (13) trifluoromethylthio; (14) ---

Signed and Sealed this

Twenty-sixth Day of October 1982

[SEAL]

Attest:

GERALD J. MOSSINGHOFF

Attesting Officer

Commissioner of Patents and Trademarks